(12) United States Patent
Mitariten et al.

(10) Patent No.: US 9,051,228 B2
(45) Date of Patent: Jun. 9, 2015

(54) LNG PRETREATMENT

(71) Applicant: Guild Associates, Dublin, OH (US)

(72) Inventors: Michael J. Mitariten, Pittstown, NJ (US); Roy Brown, Dublin, OH (US)

(73) Assignee: Guild Associates, Dublin, OH (US)

( * ) Notice: Subject to any disclaimer, the term of this patent is extended or adjusted under 35 U.S.C. 154(b) by 202 days.

(21) Appl. No.: 13/907,184

(22) Filed: May 31, 2013

(65) Prior Publication Data
US 2014/0357925 A1 Dec. 4, 2014

(51) Int. Cl.
*C10L 3/10* (2006.01)
*C07C 7/00* (2006.01)

(52) U.S. Cl.
CPC .. *C07C 7/005* (2013.01); *C10L 3/10* (2013.01)

(58) Field of Classification Search
None
See application file for complete search history.

(56) References Cited

U.S. PATENT DOCUMENTS

| 4,964,887 A * | 10/1990 | Shimatani et al. ............... 95/51 |
| 2014/0174290 A1* | 6/2014 | Sawamura et al. ............... 95/51 |
| 2014/0187838 A1* | 7/2014 | Vaidya et al. ............... 585/802 |
| 2014/0371478 A1* | 12/2014 | Schmitt et al. ............... 556/40 |

* cited by examiner

*Primary Examiner* — Tam M Nguyen
(74) *Attorney, Agent, or Firm* — Fishman & Associates, LLC.

(57) ABSTRACT

A natural gas feedstream containing contaminants such as carbon dioxide is purified by passing the contaminated natural gas stream through a membrane to remove the bulk of the contaminant, passing the purified natural gas stream to a TSA unit to remove additional contaminant from the natural gas stream to a desired specification, and regenerating the TSA adsorbent by heating the adsorbent with a heated contaminant-containing permeate stream from the membrane.

15 Claims, 1 Drawing Sheet

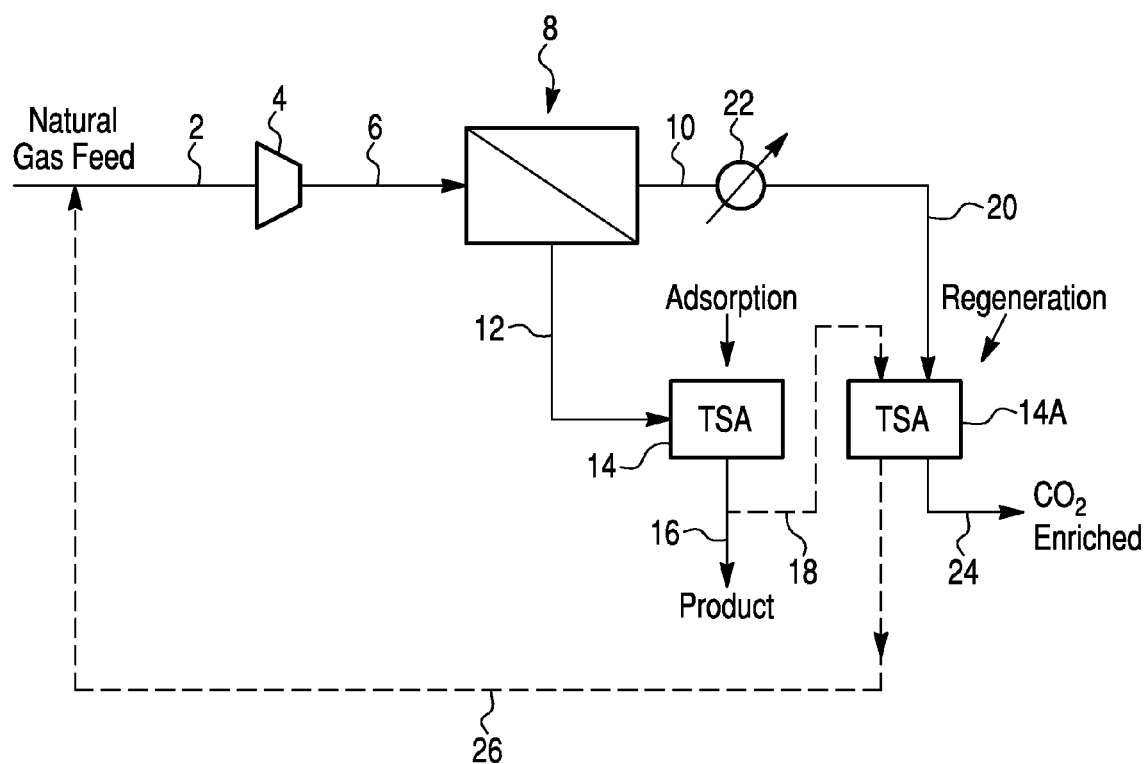

LNG PRETREATMENT

BACKGROUND OF THE INVENTION

This invention relates to a process and system for removing carbon dioxide from natural gas. More specifically, the invention relates to an integrated membrane/adsorbent system for removal of carbon dioxide from natural gas.

FIELD OF THE INVENTION

The production of LNG is well proven and growing as the world's demand for natural gas increases. While large-scale international LNG projects are well defined, in addition, small scale LNG is growing in interest.

In the production of liquefied natural gas many technology routes are used, but all such routes have in common the need to reduce the temperature of the natural gas stream to approximately −270° F. At this low temperature, certain components found in the natural gas can freeze and cause operating difficulties. Should components freeze in the natural gas liquefier, continued operation is not possible. For this reason, natural gas is pretreated to remove components subject to freezing at the LNG temperatures, which components primarily include carbon dioxide and water.

In an LNG (Liquefied Natural Gas) plant, carbon dioxide content in the feed gas stream must be reduced to 50 ppmv or less before liquefaction to avoid formation of solid carbon dioxide within the system. Commercially this can be achieved by using a solvent absorption process such as contacting the natural gas with an amine solvent to remove the carbon dioxide, which is then followed with the natural gas being sent through a molecular sieve dehydration unit to remove water down to below 1 ppmv.

Depending on the amount of carbon dioxide and the volume in the inlet gas stream, membrane processes have also been used to remove the bulk of the carbon dioxide in front of a downstream amine unit. One of the benefits of this membrane-amine hybrid system is the reduction of the size of amine column that is needed, and as well as a reduction in its energy consumption.

In many LNG plants, the water and carbon dioxide components are removed by adsorption onto one or more molecular sieve beds. Adsorption systems for LNG plants include TSA (Temperature Swing Adsorption) processes employing molecular sieves such as 4A or 13X zeolites that remove both carbon dioxide and water from natural gas streams. A growing application for a TSA process is for peak shaving of pipeline gas, where a portion of the pipeline gas is converted and stored as an LNG when demand is low. In the TSA process, the adsorbed carbon dioxide and water in the molecular sieve column are regenerated using a hot purge gas, typically from the $CO_2$-reduced product gas stream. The hot regeneration gas can be cooled and returned to the pipeline if impurity levels are acceptable or used as local fuel. The carbon dioxide removed from the adsorbent, which is not condensable at the cooler temperature, is also returned to the pipeline. An example of such a process is disclosed in U.S. Pat. No. 8,388,732, issued Mar. 5, 2013.

The adsorption of water is easier than $CO_2$ and requires less adsorbent, while the adsorption of $CO_2$ requires relatively large adsorbent quantities. This means that the larger the amount of $CO_2$ in the feed, the more adsorbent is required. The expense of the additional adsorbent to accommodate removal of larger amounts of $CO_2$ in the feed gas lessens the use of the adsorption process.

In two bed designs (one adsorbing/one desorbing) for TSA processes, the regeneration gas typically as noted above a slipstream of dry CO2-reduced product gas, can be equivalent to 60% of the feed gas when the $CO_2$ in the feed is 3 vol. % or above. For this reason, it is typical that 3% $CO_2$ in the feed is an upper limit and even this level is difficult to remove. Since a large amount of product is needed for regeneration, TSA process efficiency is degraded. It is also known in the art that three of more TSA vessels can be used, including cycles that cool a first regenerating bed and then pass the effluent to a heater for heating a second regenerating bed. Such cycle optimizations are included as part of this invention.

In general, membrane processes that use carbon dioxide-selective polymers such as cellulose acetate can not generate a residue or product stream that meets the specification levels of less than 50 ppmv $CO_2$, as the process is limited by the driving force or the $CO_2$ partial pressure across the membrane. Molecular sieve TSA processes typically can not handle a feed stream with more than 3% $CO_2$, since the size of the adsorbent beds that is required becomes too large and the necessary regeneration gas flow then becomes prohibitively large.

There exists, therefor, a need to develop an improved process or integrated process that can remove carbon dioxide and moisture to meet LNG requirements, and that can be operated with increased efficiently over what is presently achievable.

SUMMARY OF THE INVENTION

The present invention provides an integrated process for treating a natural gas stream, comprising sending a natural gas stream to a membrane unit to remove a portion of the carbon dioxide and other impurities, such as $H_2O$ or $H_2S$, from the natural gas stream, and to produce a partially purified natural gas stream. The partially purified natural gas stream is then directed to a temperature swing adsorption unit to remove carbon dioxide and produce a purified natural gas stream, having a reduced $CO_2$ content sufficient for LNG formation. A regeneration gas stream is sent to the temperature swing adsorption unit to desorb carbon dioxide from adsorbents within the temperature swing adsorption unit. The use of a membrane to remove the bulk of the $CO_2$ from the natural gas feed, allows the use of reduced amounts of adsorbent in the TSA process.

The unique aspect of this invention is that the regeneration gas stream used to desorb the $CO_2$ from the TSA adsorbent includes the permeate stream from the membrane, primarily $CO_2$, for heating the adsorbent and a slipstream of purified product gas to complete heating, if required, and flush the adsorbent bed of residual $CO_2$ left from the permeate and cool the bed. Thus, the membrane permeate stream is heated and used to heat the adsorbent bed for regeneration. In this manner, the membrane has added value by reducing the $CO_2$ concentration of the natural gas stream being fed to the TSA bed and providing the regeneration stream. Accordingly, product methane loss is significantly reduced in the regeneration process.

BRIEF DESCRIPTION OF THE DRAWINGS

The FIGURE shows an integrated membrane/adsorbent bed system for purifying natural gas.

DETAILED DESCRIPTION OF THE INVENTION

In this invention, membrane and adsorption processes are combined in an integrated process to remove $CO_2$ from a natural gas stream to 50 ppm and below. The inlet raw natural gas stream is first processed by a membrane unit to remove the bulk of the $CO_2$ from the natural gas feed and lower the $CO_2$ level by typically half or less than that of the inlet concentration. The membrane can be of a single stage or multi-stage for increasing hydrocarbon recovery. The product gas or the residue (retentate) gas from the membrane is sent to a molecular sieve TSA unit to further reduce the $CO_2$ to 50 ppmv or below. In all the embodiments of the invention, the non-condensable $CO_2$ permeate stream from the membrane unit is used to heat the adsorbent in the TSA unit for regenerating the adsorbent. A slipstream of the product gas can be used to flush the heated adsorbent, and the regeneration gas from the TSA unit can be partly recycled back to the feed and inlet of the membrane.

In general, in the integrated process of the present invention, a membrane unit is used to first treat the feed gas to lower the $CO_2$ level from at most 3% to about 1% or less, thus removing the bulk of the $CO_2$ and allowing the TSA unit to operate more effectively to remove the remaining $CO_2$ to achieve the proper specification, e.g. 50 ppmv or less for LNG production. The natural gas feed is typically treated at 300 to 1,000 psia which may require feed compression and directed to the membrane at a temperature of about 60 to 200° F. The gas permeable membrane is designed for bulk rejection of the $CO_2$ permeable component from the natural gas feedstream. The gas permeable membrane provides a methane-depleted gas stream of permeate gas rich in carbon dioxide at reduced pressure and a high pressure carbon-depleted non-permeate stream, containing a mixture of the feed constituents comprising carbon dioxide at a reduced carbon dioxide concentration relative to the feed concentration of carbon dioxide. Thus, the carbon dioxide-depleted non-permeate stream will comprise methane and carbon dioxide in a ratio, which will vary, based upon the partial pressure difference across the membrane and the flow rate of the input feed natural gas. In commercial embodiments, the non-permeate gas stream and the permeate gas stream are discharged at opposite ends of the gas permeable membrane unit, with the feed inlet positioned near the permeate gas outlet. In operation, the pressurized feed gas or natural gas stream enters the gas permeable membrane and carbon dioxide selectively permeates the membrane walls. The carbon dioxide-rich permeate gas passes through the interior of the fiber bores at reduced pressure and is delivered to the permeate gas outlet at one end of the membrane, while non-permeate gas passes to the outlet at the opposite end of the membrane. The exact structural configuration of the membrane is not a part of this invention and, thus, any known membrane structure can be utilized in the process of this invention.

The resulting partially purified natural gas feed stream as the non-permeate gas stream can optionally be cooled to about 45° C., preferably to about 35° C., more preferably to about 24° C., and even more preferably cooled to below about 5° C. Subsequent to membrane treatment and cooling, if required, the partially purified natural gas stream, which is retained by the membrane unit, is sent to a molecular sieve TSA unit to further reduce the $CO_2$ level to 50 ppmv or below. As in conventional practice, any suitable adsorbent material may be used in the TSA system of the invention. Suitable adsorbents known in the art and commercially available include crystalline molecular sieves, activated clays, silica gels, carbon molecular sieves and the like. Such adsorbent material or mixtures thereof will be understood to be suitable if the adsorbent material is capable of selectively adsorbing impurities such as carbon dioxide from a natural gas stream. The TSA adsorbent must be periodically regenerated to maintain effective separation of the carbon dioxide from the natural gas. The TSA adsorbent is regenerated by heating the $CO_2$-enriched permeate stream from the membrane and passing this heated $CO_2$-enriched stream through the TSA bed. To remove the $CO_2$ adsorbed on the bed and regenerate the adsorbent, the adsorbent is heated to a temperature of at least 250° F., preferably at least 500° F. The regeneration gas from the TSA unit, which contains the non-condensable $CO_2$, may be partly recycled back to the inlet of the membrane to reduce methane losses.

More specifically, as shown in the FIGURE, a natural gas feed 2 is shown entering a membrane unit 8 via line 6, subsequent to being pressurized by compressor 4. Carbon dioxide is selectively removed from the natural gas feed as a permeate stream 10, and the treated natural gas as retanate in membrane unit 8 is directed via line 12 to a TSA unit. In the FIGURE, the TSA unit is depicted as two units, unit 14 for adsorption and unit 14A for regeneration. In reality, the TSA unit would be a single unit, in which adsorption and regeneration take place in a sequential process. It should be understood, however, that while as noted above, the membrane unit 8 can include one or more membranes, the TSA unit can also include more than one unit 14/14A. In adsorption unit 14, the natural gas retenate from membrane unit 8, having a lower $CO_2$ content then feed 2, is further treated to reduce the carbon dioxide levels to below 50 ppm by the adsorbent in the TSA unit. The adsorbent captures carbon dioxide and allows the natural gas or methane stream to pass there through. The fully treated natural gas stream exits TSA adsorption unit 14 via line 16, and can now be sent to a liquefier (not shown).

After a certain time during the adsorption process in TSA unit 14, the adsorbent is no longer capable of efficiently selectively adsorbing the $CO_2$ from the natural gas and, accordingly, the TSA unit now must proceed to a regeneration cycle. In TSA processes, regeneration is achieved by heating the adsorbent to release the captured $CO_2$. As shown in the FIGURE, the adsorbent in the TSA unit is regenerated by directing the carbon dioxide permeate stream 10 to the TSA unit 14A via line 20. Prior to contacting the adsorbent, the permeate stream 10 is heated from membrane unit 8 in heater 22. Contact with the heated permeate stream heats the adsorbent to the desired desorption temperature. After the bed 14A is heated (in full or in part) with the membrane permeate 10, the bed can be purged with a slipstream 18 of the product gas. This product gas 8 can be used to (1) complete heating in the adsorbent, if required, (2) flush the bed of residual $CO_2$ left from the permeate and (3) to cool the bed. The bed 14A, once cooled, is now ready for another adsorption cycle and use as bed 14. A $CO_2$-enriched stream 24 leaves the TSA unit 14A. A portion of the $CO_2$-enriched stream, which may include the cooling product slipstream may be recycled to the feed 2 via line 26.

The discussion above has focused upon upgrading pipeline gas, typically containing 3% carbon dioxide or less. However, the concept of this invention can be expanded to other feedstocks, for example, natural gas streams containing other contaminants such as water or wellhead natural gas, which often contains higher levels of carbon dioxide. In each of these examples, a membrane can be used to first remove the bulk of the contaminant and a TSA system used to further minimize the contaminant in the product gas. The contaminant-containing permeate from the membrane can be heated and used to heat the adsorbent in the TSA bed for desorption and regeneration of the TSA unit.

Example 1

A natural gas stream with a $CO_2$ composition of 2% was pressurized to 715 psia at a temperature of 80° F. for reducing the $CO_2$ level and conversion to LNG. Based on the first embodiment of the current invention in the FIGURE, the gas first enters into a membrane unit to remove the bulk of $CO_2$ and the membrane retenate product gas is then sent to a molecular sieve TSA unit to remove $CO_2$ down to the 50 ppm level. The permeate gas from the membrane at 25 psia is heated to 500° F. for heating the TSA adsorbent.

TABLE

| Membrane |
| --- |
| Inlet flow = 100 Units |
| Inlet Pressure = 615 psia |
| Inlet temperature = 80° F. |
| Inlet composition: |
| $CH_4$ = 98% |
| $CO_2$ = 2% |
| Outlet flow = 85 Units |
| Outlet pressure = 605 psia |
| Outlet composition: |
| $CH_4$ = 99.3% |
| $CO_2$ = 0.7% |
| TSA |
| Outlet flow = 70 Units |
| Outlet pressure = 595 psia |
| Outlet composition: |
| $CH_4$ = 99.995% |
| $CO_2$ = 50 ppm |

Lost methane for regeneration ~15 units from membrane permeate stream used for heating the bed plus 15 units from the TSA product used for cooling the TSA regenerating bed.

The invention claimed is:

1. A process for treating a natural gas feed stream containing a contaminant comprising:
    a) passing said natural gas feed stream to a membrane unit to remove at least a portion of said contaminant from said natural gas feed stream as a permeate, and yield a partially purified natural gas stream as retenate;
    b) passing said partially purified natural gas retenate stream to a temperature swing adsorption unit containing an adsorbent to remove a further amount of said contaminant and produce a purified natural gas stream, having less contaminant than said retenate and;
    c) regenerating said temperature swing adsorption unit to desorb said contaminant from said adsorbent within said temperature swing adsorption unit by heating said permeate and using said heated permeate stream to heat said adsorbent.

2. The process of claim 1, wherein said contaminant is carbon dioxide.

3. The process of claim 2, wherein said natural gas feed stream contains at most 3% by volume of said carbon dioxide.

4. The process of claim 2, wherein said natural gas feed stream contains at most 2% by volume of said carbon dioxide.

5. The process of claim 2, wherein said natural gas feed stream is from a natural gas pipeline.

6. The process of claim 1, wherein said adsorbent within said temperature swing adsorption unit is heated to a temperature of at least 250° F. for desorption.

7. The process of claim 6, wherein said adsorbent within said temperature swing adsorption unit is heated to a temperature of at least 500° F. for desorption.

8. The process of claim 6, wherein a portion of said purified natural gas stream is used to flush the adsorbent of residual carbon dioxide after said heating.

9. The process of claim 6, wherein a portion of said purified natural gas stream is used to heat said adsorbent.

10. The process of claim 6, wherein a portion of said purified natural gas stream is used to cool said adsorbent after said heating.

11. The process of claim 3, wherein said purified natural gas stream has a $CO_2$ content of at most 50 ppm.

12. The process of claim 2, wherein said natural gas feed stream is pressurized to at least 300 psia prior to entering the membrane unit.

13. The process of claim 1, wherein more than half of the amount of contaminant is removed from the natural gas feed stream by said membrane.

14. The process of claim 13, wherein said contaminant is carbon dioxide.

15. The process of claim 11, wherein said purified natural gas stream is cooled to produce LNG.

* * * * *